United States Patent [19]

Sunano et al.

[11] Patent Number: 4,608,232
[45] Date of Patent: Aug. 26, 1986

[54] GAS SENSOR

[75] Inventors: Naomasa Sunano, Akashi; Naotatsu Asahi, Katsuta, both of Japan

[73] Assignee: Hitachi, Ltd., Tokyo, Japan

[21] Appl. No.: 399,858

[22] Filed: Jul. 19, 1982

[30] Foreign Application Priority Data

Jul. 21, 1981 [JP] Japan .................. 56-114961
Feb. 1, 1982 [JP] Japan .................. 57-13261

[51] Int. Cl.[4] .......................... G01N 27/12
[52] U.S. Cl. .......................... 422/88; 73/23; 324/65 R; 338/34; 338/35; 422/98
[58] Field of Search .............. 422/98, 94, 88; 436/151, 152; 204/426, 429, 1 Y, 1 S; 338/34, 35; 324/65 R; 73/23 R

[56] References Cited

U.S. PATENT DOCUMENTS

| 3,558,280 | 1/1971 | Panson et al. ............ 422/90 |
| 3,951,603 | 4/1976 | Obayashi et al. .......... 422/78 X |
| 4,044,601 | 8/1977 | Sakurai et al. ........... 422/98 X |
| 4,221,827 | 9/1980 | Parry et al. ............. 422/98 X |
| 4,224,280 | 9/1980 | Takahama et al. ......... 422/98 |
| 4,265,930 | 5/1981 | Shinohara et al. ........ 204/429 X |
| 4,276,202 | 6/1981 | Schmidberger et al. . |
| 4,359,374 | 11/1982 | Sano et al. ............. 204/429 |

FOREIGN PATENT DOCUMENTS

| 0017502 | 10/1980 | European Pat. Off. . |
| 0043755 | 1/1982 | European Pat. Off. . |
| 2746381 | 4/1978 | Fed. Rep. of Germany ........ 422/98 |
| 1562623 | 3/1980 | United Kingdom . |
| 2037432 | 7/1980 | United Kingdom . |

Primary Examiner—Arnold Turk
Attorney, Agent, or Firm—Antonelli, Terry & Wands

[57] ABSTRACT

Gas sensor which is constructed of an electrically insulating base, electrodes formed on said base, and a gas sensitive film formed on the surface of said base at a portion where it detects a gas to be sensed, e.g., an oxygen gas. The gas sensor of the present invention is characterized in that the gas sensitive film is a thermal-sprayed film which is made of an oxide having a perovskite structure. The thermal-sprayed film has its surface formed with fine cracks to have its effective surface area increased so that the response is speeded up. Moreover, the thermal spraying process is so effected during the formation of the oxide film that an impurity to adversely affect the reliability may be avoided from being mixed.

The gas sensor may have said gas sensitive film coated with a ceramic material so that is performance may be further improved while protecting the gas sensitive film. Furthermore, it is also effective to add another sensor with the electrically insulating base being commonly used.

12 Claims, 18 Drawing Figures

GAS SENSOR

BACKGROUND OF THE INVENTION

1. Field of the Invention

The present invention relates to a novel gas sensor and, more particularly, to a gas sensor which is suitable for detecting and controlling the oxygen concentration or the humidity in a gas.

2. Description of the Prior Art

Recently, there has been desired the development of a sensor for detecting the oxygen concentration or the humidity in the atmosphere or in the exhaust gas of an automobile or the like, especially, a safety device for (1) controlling the excess air ratio of a burning device such as a gas burner or a petroleum burner, (2) preventing the imcomplete combustion and the misfire, and (3) a highly reliable and inexpensive oxygen concentration detecting sensor which can be applied for the control or the like of the excess air ratio by detecting the oxygen concentration in the exhaust gas of the automobile.

As the sensor of this type, there has been proposed according to the prior art an oxygen concentration cell system which uses stabilized zirconia, ceria or the like. However, this system has difficulties in the design and installation of the structure required for the system has a defect that it cannot be stably operated at a temperature equal to or lower than 350° C. This defect is eliminated by the development of a sensor which is made of an oxide having a perovskite structure and which makes use of the change in the resistance due to the difference in the oxygen concentration. The perovskite structure oxide is a crystal of such a double oxide that is expressed by a general formula: $ABO_3$. However, the characteristics of a sensor of this type are greatly determined by the composition of the oxide and are largely influenced by the presence of a minute quantity of an impurity. Therefore, the base of the sensor of this type according to a prior art is prepared by a sintering process or by the calcining process wherein a mixture of the oxide with a vitreous substance is used so that the base may not be contaminated during the preparing process.

The sintering process is a method (references should be made to U.S. Pat. No. 4,044,601), by which material powders are formed into the shape of a sensor base or formed into slurry and applied to an electrically insulating base before the powders are sintered. According to this sintering process, a bulk having a certain size is prepared and is cut into predetermined thin and small pieces. Generally speaking, however, an oxide having the perovskite structure is so brittle because of insufficient sintering properties that the sensor using this structure has a low speed of response and has short durability. Moreover, in the sintering process it is difficult to form fine cracks in the structure which can enlarge the apparent effective surface area and consequently the sensor fails to have a high speed of response.

On the other hand, the calcining process using glass powders is a method (reference should be made to Japanese Patent Laid-Open Publication No. 56-31631), by which a mixture of the perovskite type oxide of material powders with glass powders is prepared into slurry and formed into a predetermined shape or is applied to a base before it is calcined. This calcining process has the problems that the characteristics of the product are dispersed over a wide range as a result of the mixture containing an impurity and that yield the characteristics of the product after a long use are deteriorated. Moreofer, since the surface is made so remarkably smooth by adding the glass powders that the apparent surface area thereof is reduced, the speed of response is lowered similarly to the product of the sintering process.

SUMMARY OF THE INVENTION

It is, therefore, an object of the present invention to provide a highly reliable and responsive gas sensor, which is less contaminated by the presence of an impurity so that it has stable characteristics, for use as an oxygen sensor, a flame sensor or a humidity sensor.

According to a first feature of the present invention, there is provided a gas sensor which comprises: an electrically insulating base; electrodes formed on the base; and a gas sensitive film formed on the surface of said base at a portion, where the film detects a gas to be sensed, and which is characterized in that said gas sensitive film is a thermal-sprayed coating film made of an oxide having a perovskite structure.

According to one aspect of the present invention, there is provided a gas sensor which is characterized in that the gas sensitive film made of the thermal-sprayed coating film of the oxide having the perovskite structure is covered with a ceramic material.

The present invention also provides, a gas sensor which is characterized in that a pair of electrodes are arranged on each of the exposed surface and back of said electrically insulating base, in that a thermal-sprayed coating film of the oxide having the perovskite structure is formed as to be in an electric contact with one pair of the electrodes; whereas a film having thermistor and/or heater characteristics is formed to be in electric contact with the other pair of electrodes thereby to provide a composite or multifunction sensor.

According to another aspect of the present invention, there is provided a sensor wherein a pair of electrodes are arranged on each of the surface and back of said electrically insulating base, and in that a thermal-sprayed coating film of an oxide having a perovskite structure is formed to be in electric contact with one pair of the electrodes of one pair and is covered with a ceramic material; whereas a film having thermistor and/or heater characteristics is formed to be in electric contact with the other pair of electrodes thereby to provide a composite sensor.

Further the present invention provides a sensor wherein the gas sensitive film is an oxygen sensitive film which is made of a thermal-sprayed coating film of an oxide having a perovskite structure so that an oxygen concentration is detected by making use of the change in the resistance of the oxygen sensitive film due to the difference in the oxygen concentration of a gas.

Another feature of the gas sensor of the present invention, is in that the gas sensitive film is a humidity sensitive film which is made of a thermal-sprayed coating film of an oxide having a perovskite structure so that humidity is detected by making use of the change in the resistance of said humidity sensitive film due to the change in the humidity of a gas.

Thermal-Sprayed Coating Film of Oxide

The gas sensor of the present invention is constructed by forming an electrically insulating base with a surface film which is made of an oxide having a perovskite structure and which is formed with fine cracks. This film is prepared by the thermal spraying process. The fine cracks are effective to effect an increase in the effective surface area of the film. A film having its electric resistance changed one to four orders with the change in the oxygen concentration or the humidity is preferred as the gas responsive film, and the oxide having a perovskite structure is the most referred. A P-type semiconductor is preferred especially as the material for detecting, sensing and responding to a combustion state. As that P-type semiconductor, there can be enumerated $LaNiO_3$, $La_2CuO_4$, $CeTiO_3$, $PrTiO_3$, $NdTiO_3$, $LatiO_3$, $LaCrO_3$, $La_{1-x}Sr_xCoO_3$ ($0.1 \leq x \leq 0.5$) and $La_{1-x}Sr_xVO_3$ ($0 \leq x \leq 0.5$). The P-type perovskite structure has its resistance increased, in case the gas responsive portion of the gas sensor is broken, similarly to the condition occurring with a shortage of air so that a safety operation such as for preventing misfire can be effected.

The oxide having the perovskite structure is prepared by a general process to have a desired composition and it is then pulverized into fine powders. The size of the particles is especially important. The particles are preferred to have a size equal to or smaller than about 25 $\mu$m or desirably a size of about 0.1 to 5 $\mu$m. The size is important because the speed of response and the sensitivity of the sensor using the oxide of a perovskite structure are dependent upon the thickness of the film and a state of the fine cracks. The thickness of the film is desired as small as possible within a range of about 1 to 500 $\mu$m. On the other hand, the fine cracks are desired to have a size equal to or smaller than several microns.

The thermal-sprayed coating film may be composed mainly of the oxide having perovskite structure and may contain another ceramic material.

Thermal-Spraying Process

A variety of methods have been investigated and it has been found that it is the most desirable to form a number of fine cracks in the surface of a film by the plasma spray coating of powders having a certain range of particle size. Within a range of thickness from several microns to several tens of microns, a higher speed of response and a higher sensitivity are exhibited as number of fine cracks is increased. For the particle size of 10 to 44 $\mu$m to be used in a general thermal-spraying process such as the thermal-spraying process using the oxygen-acetylene flame, for example, it is more difficult than the plasma spray coating process to form such uniform fine cracks and a thin film that can exhibit stable characteristics. As the stabilizing gas for the plasma spray coating process, there is generally used a gas mixture of argon, nitrogen and hydrogen. In the present invention, however, that gas mixture may desirably contain oxygen. This is because a complex oxide may be reduced during the thermal-spraying operation by the hot plasma to change the characteristics. A film having stable characteritics is formed by the spraying operation in an atmosphere containing oxygen. Since, at this time, the film thickness exerts influences upon the characteristics, as has been described hereinbefore, it is desired to conduct the spraying operation in a manner to make the thickness as small as possible within the range of about 1 to 500 $\mu$m, preferred to be less than 10 $\mu$m.

When in the spraying operation, it is preferred to preheat the electrically insulating substrate to a temperature equal to or higher than 500° C. and to hold it at a high temperature during the spraying operation. By this procedure, it is made possible to form a number of cracks in the surface of the film and to ensure the adhesiveness between the base and the oxide film thereby easily enhancing the durability of the film.

Electrically Insulating Base

In the present invention, electrically insulating base may preferably be made of a highly thermally conductive material, which is stable at a high temperature, such as a material selected from the group consisting of alumina and silicon carbide. The base is desired to be made as a thin plate. The thickness of the thin plate may be about 0.5 mm or less and is preferred to be less than 0.3 mm. This thickness is important because the heat conductivity becomes lower with an increase in the thickness of the thin plate so that the thin plate is liable to be formed with relatively large cracks, if the base is excessively thick, due to the thermal shocks. Such shocks are exemplified by abrupt heating to a high temperature or by repetitions of the heating and cooling operations, thereby causing the durability of the film to be deteriorated.

It is desirable for the electrically insulating base to have its surface either made porous at least beneath the gas sensitive film, where the aforementioned gas sensitive film is formed, or formed with the fine cracks at least beneath the gas sensitive film. The surface of electrically insulating base may be made coarse to a desired extent when it is prepared. In an alternative, the electrically insulating base may have its surface formed with a coarse film by a thermal-spraying process or the like. For example, the electrically insulating base is covered with a thin film of a spinel oxide such as alumina or alumina-magnesia or the thin film is formed with fine cracks. If a gas sensitive film is formed on the base, i.e., an oxide film which has its electric resistance remarkably changed in a gas atmosphere, it is possible to produce a gas sensor which is excellent in durability and which is freed of the problem having the film peeled therefrom.

By making the surface of the electrically insulating base coarse in the aforementioned way, the base temperature during the spraying operation can be held at a lower level than the aforementioned one (which should be referred to that of the thermal-spraying proces), and an adhesive oxide film having less peeling and wear during the use can be formed.

Ceramic Coating Film on Thermal-Sprayed Film of Oxide

If the sprayed film of the oxide is coated with a ceramic film, the sensor can have its speed of response and its durability further improved. As the ceramic film, there is desired an oxide film which has an electric resistance substantially equal to or higher than that of the group consisting of alumina, silicon carbide and zirconia and which has a reactivity substantially identical or lower than that of the same material. For example, the alumina is suitable for the material of the coating film. Incidentally, a ceramic coating film on the surface is desired to be formed with the fine cracks or to be made porous. The film on the surface functions not only as protecting the inner oxide film from wear during use or to provide a catalyzer but also to stabilizing the change in a resistance. Incidentally, similar effects can be attained by mixing the alumina or the like with fine powders of another oxide thereby to form a surface coating film.

On the other hand, in case the gas sensitive film is a thermal-sprayed film of an oxide having a perovskite structure, the surface ceramic film may be made of a mixture of powders of a perovskite structure oxide with powders of inert glass. With the use of such mixture, the inner gas sensitive film is less peeled, and the electric resistance can be stabilized while reducing aging. For example, a glass powder composition which is composed of $SiO_2(80\%)$, $B_2O_3(12.7\%)$, $Na_2O_3(3.4\%)$, $Al_2O_3(2.3\%)$, $Fe_2O_3(0.03\%)$ and $K_2O(0.04\%)$ is sufficiently rinsed with water and is mixed with powders of an oxide having a perovskite structure. The resultant mixture is fixed to overlie the thermal-sprayed film of the perovskite structure oxide which contains a small quantity of powdered glass to form a protecting coating. Then, it is possible to form a stable and durable film which shows no appreciable change in characteristics due to aging. Especially, this two-layered structure is suitable for the gas sensor which is used as a flame sensor.

Composite Sensor

Attempts have been made to use an electrically insulating base as the common base of two kinds of sensors. One is the gas sensor which uses the thermal-sprayed film of the oxide; whereas the other is the sensor which has for example thermistor and/or heater characteristics, for example.

For example, if a gas sensor and a high temperature resistance sensor are formed on a common base, the output of the former sensor can be corrected by that output of the latter sensor, which is measured under the common condition. The gas sensor and the high temperature sensor have been thought as elements having different functions. Therefore, if they are integrally combined to afford a plurality of functions, waste is accordingly reduced to lead to a reduction in cost. Moreover, the receiving side is also simplified to increase the cost reduction. Also, since simultaneous detections are made possible in an identical atmosphere, a variety of applications can be found in addition to the mutual correction of the sensors. Incidentally, the base may have both its sides equipped with the aforementioned two gas sensitive films.

BRIEF DESCRIPTION OF THE DRAWINGS

In FIGS. 6, 7, 8 and 9 illustrate the constructions of gas sensors according to Example 2 of the present invention.

PREFERRED EMBODIMENTS OF THE INVENTION

The present invention is further described hereinafter by way of the embodiments thereof, but the invention is in no way limited by these embodiments.

EXAMPLE 1

Figure 1:
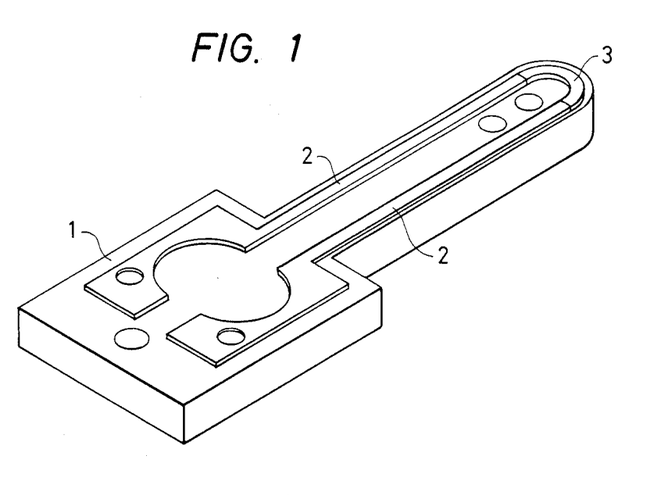
FIGS. 1 and 2 are perspective views showing gas sensors according to Example 1 of the present invention.

FIG. 1 shows one example of the oxygen sensor according to the present invention, in which an electrically insulating base 1 of alumina has its surface baked to form printed platinum electrodes 2. An oxide film 3 having a thickness of about 5 $\mu$m is so formed as to be in an electric contact with the electrodes by thermal-spraying powders (having a particle size of 0.1 to 2 $\mu$m) of an oxide having a perovskite structure that is composed mainly of $LaNiO_3$ by the use of a plasma flame containing oxygen. The oxide film 3 has its surface formed with cracks having a size equal to or smaller than 0.2 $\mu$m.

Figure 2:
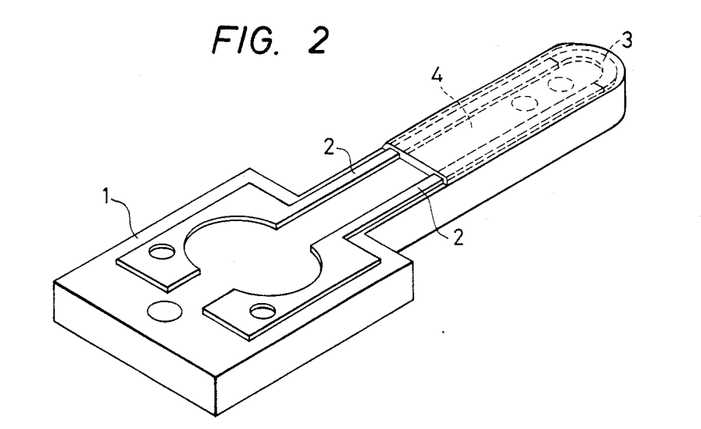

On the other hand, FIG. 2 shows another example of the oxygen sensor according to the present invention, and this example is different from that of FIG. 1 in that the oxide film 3 has its surface coated with a protecting film 4. This protecting film 4 is prepared by the thermal-spraying process and is formed with a number of cracks having a size of about 0.5 $\mu$m.

The oxygen sensor of FIG. 2 was set in a propane flame so that the change in its electric resistance was measured using the excess air ratio as a parameter. Incidentally, the results are plotted in FIG. 3. The excess air ratio "$\mu$" of this invention can be expressed as follows; $\mu = A/Ao$ where A ($Nm^3$) is an amount of air that is actually consumed for complete combustion of fuel and Ao ($Nm^3$) is a theoretical amount of air required for a complete combustion of fuel. The resistance is changed around three orders about the position of an excess air ratio of 1.05. Specifically, as the excess air ratio is increased for the temperature range of 400° to 900° C., the resistance is reduced in accordance with an exponential function. The phenomena thus described are reversible so that they are repeated with a high reproducibility.

Next, the change in the resistance for the respective excess air ratios was measured over a wide range of the temperature in the flame from 400° to 900° C. The results are plotted in FIG. 4. The experimental conditions of the respective curves are tabulated in Table 1:

TABLE 1

| Curve i | A ≈ 0.8 | Curve iv | A ≈ 1.05 | Curve vii | A ≈ 1.07 | Curve x | A ≈ 1.20 |
|---|---|---|---|---|---|---|---|
| Curve ii | A ≈ 1.0 | Curve v | A ≈ 1.055 | Curve viii | A ≈ 1.10 | Curve xi | in Air |

TABLE 1-continued

Curve iii  A ≈ 1.04    Curve vi  A ≈ 1.06    Curve ix  A ≈ 1.15

A: Excess Air Ratio

Figure 3:
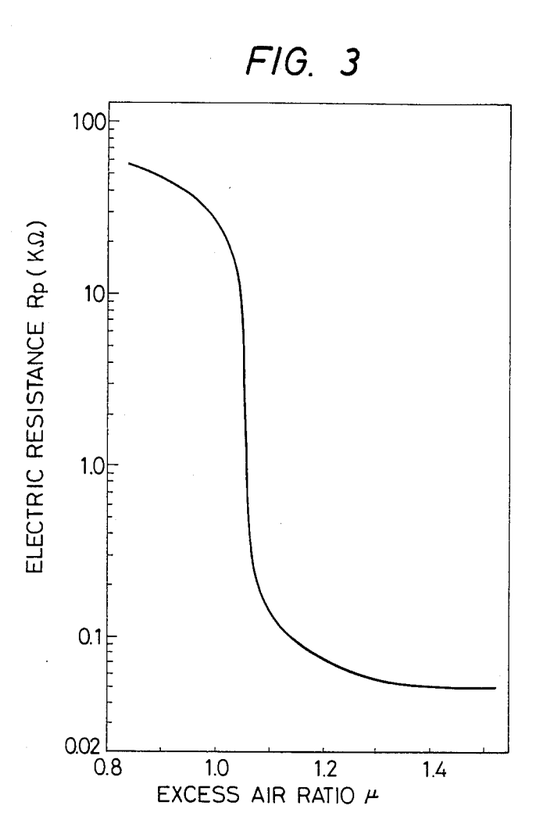
FIGS. 3, 4 and 5 are diagrams illustrating the excess air ratio characteristics of the gas sensors of Example 1 of the present invention.
Figure 4:
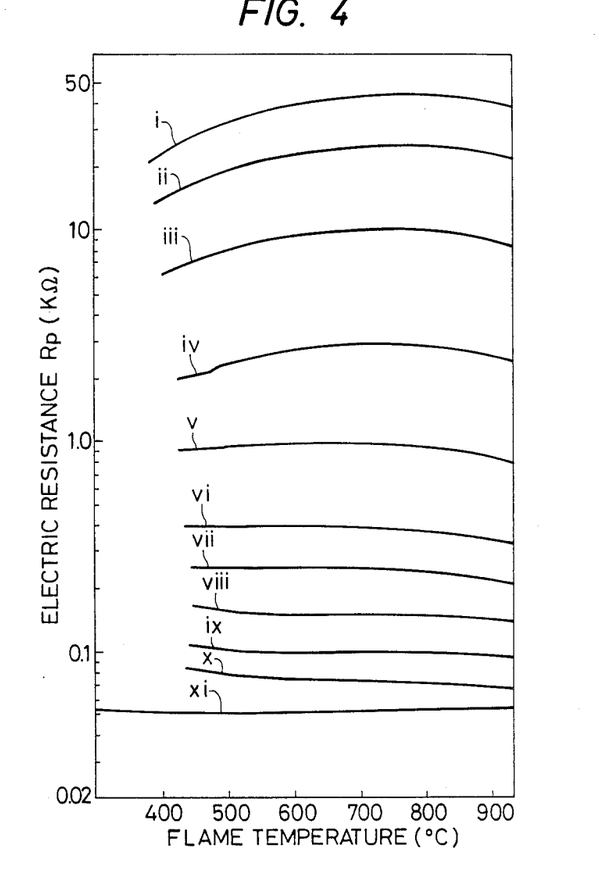

The characteristics illustrated in FIGS. 3 and 4 had similar tendencies either in case they were examined by using the oxygen sensor of FIG. 2 in place of the oxygen sensor of FIG. 1 or in case the film of the perovskite structure oxide is made of $LaCuO_4$, $CeTiO_3$, $PrTiO_3$, $NdTiO_3$, $LaTiO_3$, $LaCrO_3$, $La_{1-x}Sr_xCoO_3$ or $La_{1-x}Sr_xVO_3$.

Next, as shown in FIG. 1, when a film of $LaNiO_3$ was formed as to be in electric contact with the platinum electrodes which had been baked upon the alumina base, the following thermal-spraying conditions and structures were adopted:

(a) The base was preheated to 100° C., and $LaNiO_3$ was sprayed.

(b) The base was preheated to 700° C., and $LaNiO_3$ was sprayed.

(c) After the base had been preheated to 100° C. and alumina (having a particle size of 5 to 37 μm) had been sprayed to have a thickness equal to or smaller than 10 μm, the $LaNiO_3$ was sprayed.

The thicknesses of the $NaNiO_3$ films formed by the processes (a), (b) and (c) were between 5 to 15 μm.

(d) After the $LaNiO_3$ film had been formed similarly to the process (c), the base was coated with the alumina (having the same particle size as the above-identified range) to have a thickness ranging from 5 to 20 μm.

(e) The base was preheated to 200° C., and a mixture of the $LaNiO_3$ and the alumina (at a weight ratio of 50:50) was sprayed to form a film having a thickness of 20 μm.

(f) After the complex oxide had been formed by the process (a) or (b), the base was coated on its surface with the spinel oxide of $Al_2O_3$ and MgO having a thickness of 5 to 20 μm.

The test pieces thus produced were subjected to repeated tests, in which the test pieces were heated for five seconds to 900° C. by a propane flame, abruptly cooled down to a room temperature and held for five minutes, one hundred thousand times. As a result, the sample (a) was worn at a relatively early time from its surface layer until it could not be used. For the characteristics after the trials of the one hundred thousands times, the sample (d) was the most excellent, followed by the samples (e), (c) and (b) in this order.

Figure 5:
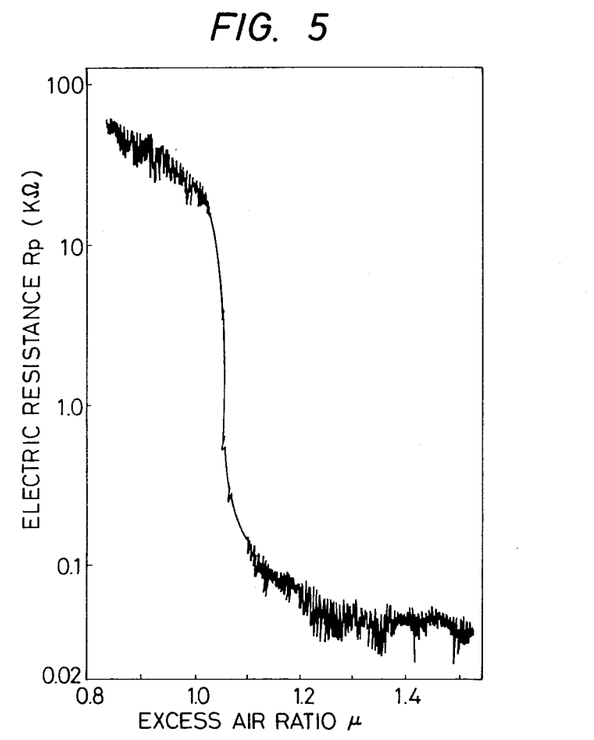

FIG. 5 is a graph illustrating the change in the resistance in accordance with the excess air ratio, of the samples (a), (b) and (c), which are not formed with the stabilized oxide film on the complex oxide film. In case there is no stabilized oxide film on the surface, the change in the resistance is fluctuated due to the external factors after a long use. That change prevented by that stabilized film.

EXAMPLE 2

Figure 6:
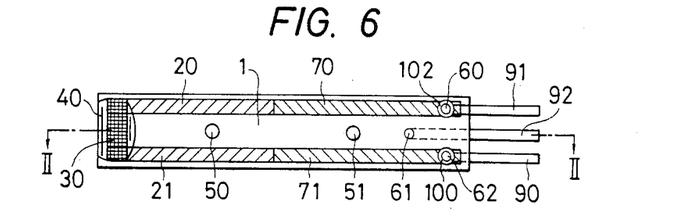
FIG. 6 is a top plan view.
Figure 7:
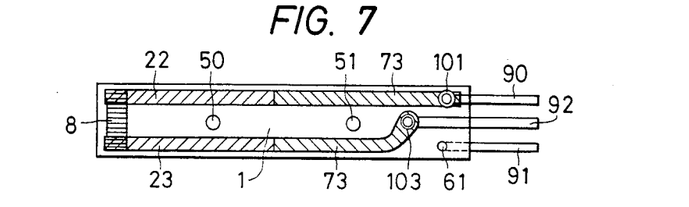
FIG. 7 is a back elevation of FIG. 6.
Figure 8:
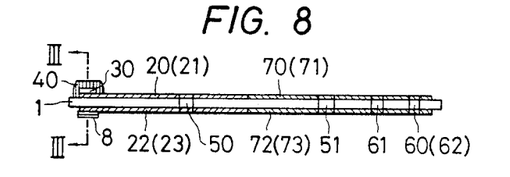
FIG. 8 is a section taken along line II—II of FIG. 6.
Figure 9:
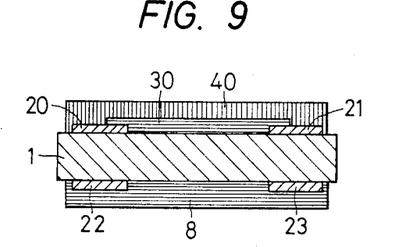
FIG. 9 is a section taken along line III—III of FIG. 8.

FIGS. 6 to 9 show an example of the flame sensor according to the present invention. Of these: FIG. 6 shows the sensor plane (which is taken at one side of the base) on that side which senses the gas (i.e., mainly the oxygen concentration); and FIG. 7 shows the sensor plane (whcih is taken at the other side of the base) on that side which senses humidity. Moreover, FIG. 8 is a sectional side view taken along line II—II of FIG. 6; and FIG. 9 is an enlarged sectional view showing the vicinity of the sensitive element and taken along line III—III of FIG. 8.

As is apparent from these figures, the flame sensor according to this Embodiment is equipped on both the sides of the electrically insulating base with sensor mechanisms, one of which is a gas sensor mechanism using the gas sensitive film coated further with the protecting coating.

In the electrically insulating base (which is a refractory porcelain in the present Embodiment) shown in those Figures: numerals 50 and 51 indicate holes for fixing pins; numerals 60, 61 and 62 indicate holes for lead pins; numerals 20, 21, 22 and 23 indicate printed platinum electrodes; numeral 30 indicates a thermal-sprayed film made of a perovskite type oxide; numeral 40 indicates a mixed film of that perovskite oxide and intert glass; numerals 70, 71, 72 and 73 indicate refractory metal film leads containing silver (i.e., calcined palladium-silver films); numeral 8 indicates a thermistor film; numerals 90, 91 and 92 indicate refractory gold film lead pins which are connected with the one-side terminals of the aforementioned refractory metal film leads 70 to 73; and numerals 100, 101, 102 and 103 indicate soldering materials which fixedly solder the refractory metal lead pins 90 to 92 and the refractory metal film leads 70 to 73 in a hydrogen flame. Incidentally, it is also effective to form a clacined platinum resistive film in place of the thermistor film 8. If the calcined platinum resistive film is used, the function of a heater can be exhibited.

First of all, two pairs of the printed platinum electrode films 20, 21, 22 and 23 are calcined at about 1350° C. on the surface of a alumina porcelain base. Next, the fine powders of a sintered substance, which is composed in weight percentage of $La_2O_3(26.5\%)$, $Cr_2O_3(10.4\%)$, $SnO_2(21.5\%)$, $TiO_2(11.8\%)$, $CuO(9.1\%)$, $Bi_2O_3(2\%)$, $SiO_2(6.3\%)$, $CaCO_3(8.2\%)$ and $Al_2O_3(4.3\%)$, are sufficiently rinsed and calcined as to be in an electric contact with the electrodes 22 and 23 thereby to form the oxide thermistor film 8 which has high temperature thermistor characteristics. Even if the temperature sensitive film thus prepared is exposed to a flame (at a temperature not exceeding 1100° C.), its aging is not appreciable. Next, the powders of an oxide having the perovskite structure (e.g., $LaNiO_3$), which have been sufficiently rinsed with water, are sprayed to coat the area between the platinum electrode films 20 and 21 by the use of a plasma (in conformity to the process of the Example 1). On the film thus prepared, moreover, there are calcined both glass powders, which have been sufficiently rinsed with water and which are composed in weight percentage of $SiO_2(80\%)$, $B_2O_3(12.7\%)$, $Na_2O_3(3.4\%)$, $Al_2O_3(2.3\%)$, $Fe_2O_3(0.03\%)$, $K_2O(0.04\%)$, and the remainder (1.53%), and the powders of the oxide having the perovskite structure. Here, the protecting film has its surface made coarse after it has been formed.

Figure 10:
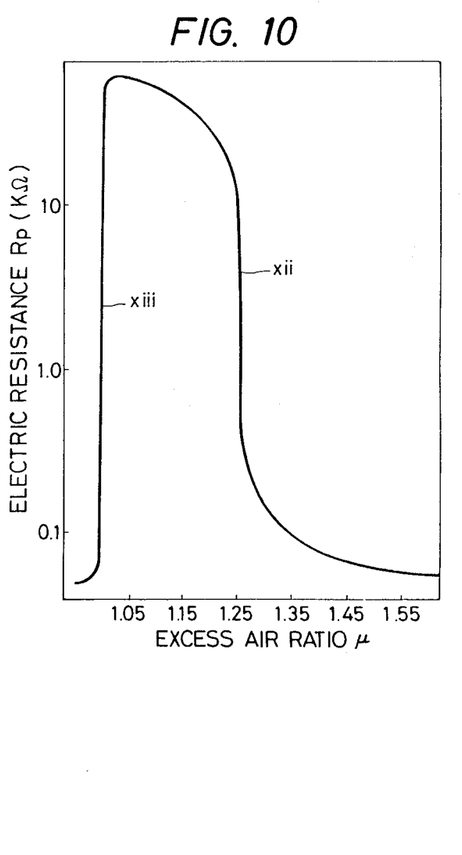
FIGS. 10 and 11 are diagrams illustrating the excess air ratio characteristics of the gas sensor of Example 2 of the present invention.

FIG. 10 illustrates the characteristics of the flame sensor of the present Embodiment in a flame (at 700° to 800° C.), in which the abscissa indicates an air-fuel ratio A whereas the ordinate indicates an electric resistance $R_P$. Curves xii and xiii correspond to abruptly changing zones, which are shifted in dependence upon the sintering temperature and the composition.

Next, the changes of the sensor using the P-type oxide having the perovskite structure were measured for the respective excess air ratios over a wide range of the temperature in the flame from 400° to 900° C. in a similar manner to the Example 1. The results are plotted in FIG. 11. The experimental conditions of the respective curves are tabulated in Table 2:

TABLE 2

| Curve xiv | $A \approx 1.0$ | Curve xvii | $A \approx 1.25$ | Curve xx | $A \approx 1.27$ | Curve xxiii | $A \approx 1.40$ |
|---|---|---|---|---|---|---|---|
| Curve xv | $A \approx 1.2$ | Curve xviii | $A \approx 1.255$ | Curve xxi | $A \approx 1.30$ | Curve xxiv in Air | A: Excess Air Ratio |
| Curve xvi | $A \approx 1.24$ | Curve xix | $A \approx 1.26$ | Curve xxii | $A \approx 1.35$ | | or $A < 1.0$ |

Figure 12:
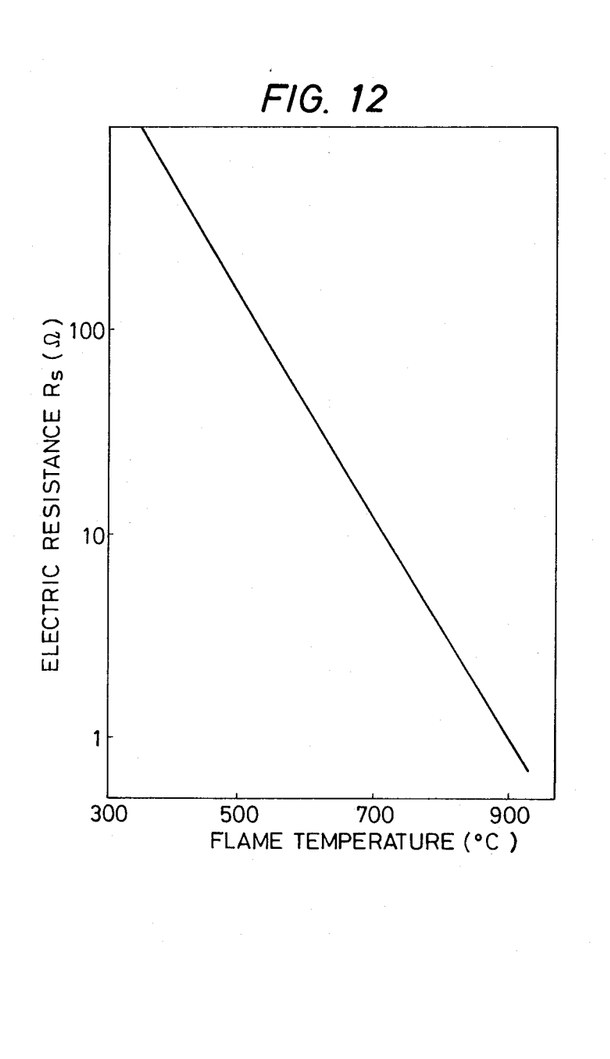
FIG. 12 is a characteristic diagram illustrating the change in the electric resistance of such a thermistor film in a flame as commonly uses the substrate of a gas sensitive film in Example 2 of the present invention.

FIG. 12 illustrates one example of the characteristics of the oxide thermistor film 8, in which the abscissa indicates the temperature of the flame whereas the ordinate indicates the electric resistance of the oxide thermistor film.

Figure 13:
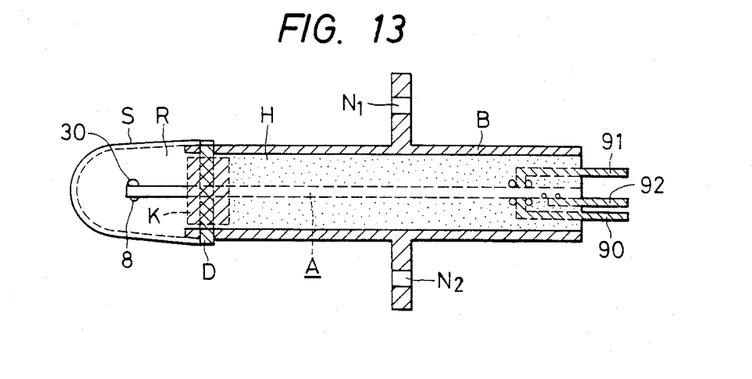
FIGS. 13 and 15 are views illustrating the examples of systems, in which gas sensors of the present invention and several parts are assembled together

FIG. 13 shows an example of the applications of the flame sensor of the present Embodiment, in which those portions indicated at the same reference numerals of FIGS. 6 to 9 are the same as those. Letter A indicates the flame sensor element of FIGS. 6 to 9; letter B indicates a refractory metal case; letter D indicates a refractory metal pin; letter H indicates refractory cement; letter K indicates a refractory percelain insulating support; letters $N_1$ and $N_2$ indicate mounting holes (on another system); letter S indicates a refractory metal net; and letter R indicates a space. Thus, the element A can be fixedly fitted in the metal case B through the refractory porcelain insulating support K by means of the refractory metal pin D and solidified (at a room temperature) by the action of the refractory cement H.

The measurements of the operations of the flame sensor thus practised are exemplified in the following. In the propane combustion flame, the characteristics of the perovskite structure oxide film 30 behave, as shown in FIG. 10, such that the electric resistance is abruptly increased above three orders in the vicinity of an excess air ratio of 1.2 until it gradually reaches its maximum in the complete combustion range. However, if the excess air ratio is further reduced to the vicinity of 0.95, its value is abruptly reversed (about three orders) thereby to indicate that the imcomplete combustion carbon is detected. The response is reversible, and the speed of response at a curve xii is expressed at a unit of millisecond whereas that at a curve xiii is expressed at a unit of minute. On the other hand, moreover, one example of the characteristics of the oxide thermistor film 8 having another function is completely independent of the excess air ratio, but is dependent upon only the temperature in the flame, as illustrated in FIG. 12, and the characteristics themselves are expressed in accordance with an exponential function with respect to the reciprocal of the temperature.

The effect of the integrated two sensors makes it possible to discriminate whether the two abruptly changing zones are excessive or short of the air in addition to the effects of the simple mounting and low price. In addition, if the heater film is used in place of the thermistor film 8, the sensor is radiated to shift the sensed temperature to a lower side. The formation of the mixed film of the perovskite oxide and the inert glass upon the perovskite oxide film brings an additional effect that the lifetime (i.e., the duration) can be improved.

The characteristics of the oxide having the perovskite structure are made, as shown in FIG. 10, such that the abruptly changing point of the N-type resistor is located in the vicinity of the excess air ratio of 0.95 thereby to inform that the complete combustion is effected in only the zone, in which the resistance of the gas sensor is high. As a result, the sensor thus far described can find a remarkably wide variety of applications if its application control system is taken into consideration by means of such an equivalent circuit as is shown in FIG. 14.

Figure 14:
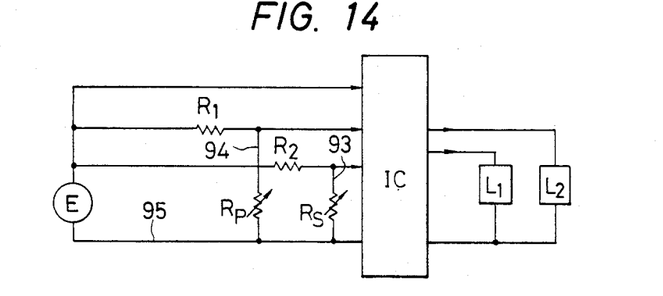
FIG. 14 is an equivalent circuit diagram showing an example of an electric circuit which comprises the gas sensors of Example 2 of the present invention.

FIG. 14 shows the equivalent circuit which exemplifies the electric circuit to which the flame sensor of the present embodiment is applied. Letter E indicates a power source; letters $R_1$ and $R_2$ indicate fixed resistors; letters IC indicate a conversion circuit; letters $L_1$ and $L_2$ indicate loads; and letters 93, 94 and 95 indicate the positions on the extensions of the lead pins 90, 91 and 92 of FIGS. 6 to 9, respectively.

Figure 11:
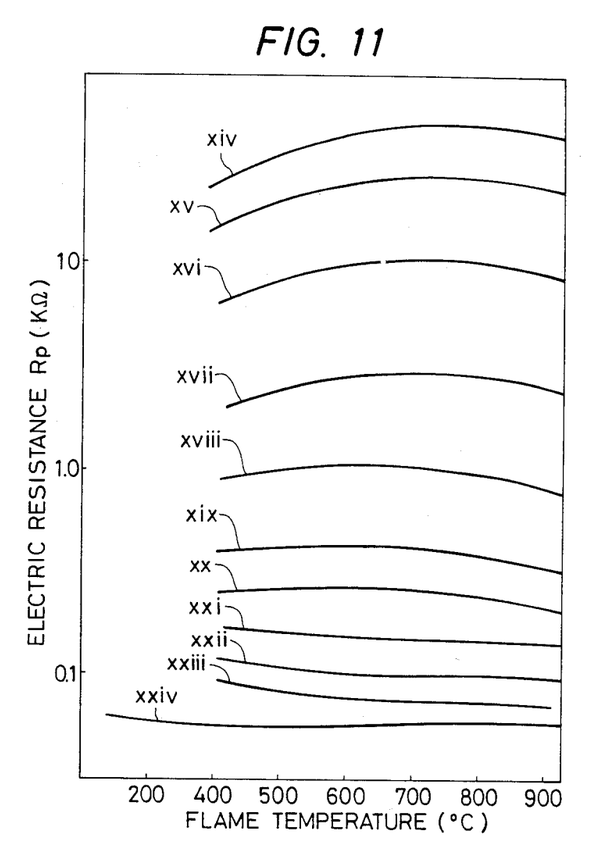

Moreover, letters $R_P$ indicate an electric resistance of the thermal-sprayed film made of the oxide having the perovskite structure and which is positioned in the flame so that its electric resistance is reverisbly changed with the characteristics shown in FIGS. 10 and 11 in accordance with the burning state. Letters $R_s$ indicate the electric resistance of the oxide thermistor film 8, which is linearly changed in a reversible manner in accordance with the reciprocal of the temperature, as shown in FIG. 12. Therefore, the loads $L_1$ and $L_2$ can be operated by the program which corresponds to the changes in the resistances $R_s$ and $R_p$.

Thus, according to the present invention, it is possible to simultaneously detect the new function, the temperature of the flame, and the burning state (mainly, the oxygen concentration), and to detect that the complete combustion is being effected at the zone having the high resistance of the gas sensitive portion. The judgement whether the abruptly resistance changing zone belongs to the region having a low or high excess air ratio can be easily determined in view of the value (which is accompanied by the change in the burning flame temperature) of another temperature sensitive sensor.

EXAMPLE 3

Figure 15:
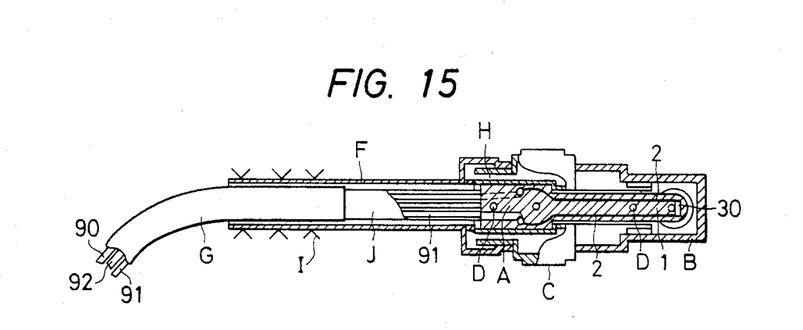
Figure 17:
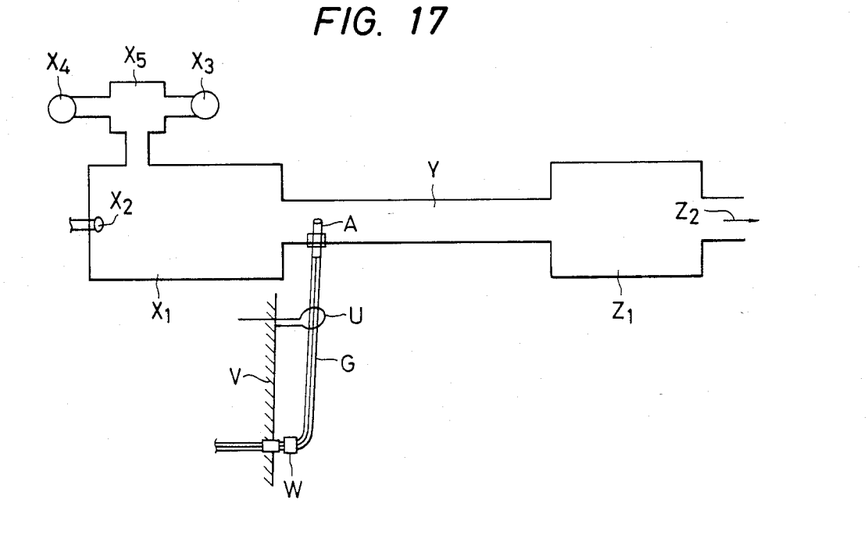
FIG. 17 is a schematic view showing an example in which the gas sensor of the present invention is incorporated into an internal combustion engine.

FIG. 15 is a sectional view showing the mounting structure of the oxygen sensor in case this sensor is mounted at a place of high vibrations, e.g., on an automobile. The oxygen sensor to be used here is the same as that of the Example 1 shown in FIG. 1 or 2. The sensitive element A is equipped with a refractory metal pin D, refractory cement H and a caulking member I so as to connect and fix a nut body C of SUS 304 metal, a holes metal cover B of SUS 304 metal, a metal (e.g., brass) connector F and a silicon cable G. This cable G is partially led out to the outside through three-holded alumina tube J so as to ensure the insulating and refractory purposes such that one leading end is electrically connected with the other terminal of the platinum electrode 2 of the sensitive element A. The metal connector F and the SUS 304 metal nut body C are mechanically connected by means of the screws. The sensor thus equipped with the jig is thermally and mechanically durable. The sensor can be applied to the internal combustion engine if it is attached, as shown in FIG. 17.

In the case of the automotive sensor, the operations at an idling low temperature range can be effected at a constant temperature if the sensor is combined with and heated by a heater.

EXAMPLE 4

Figure 16:
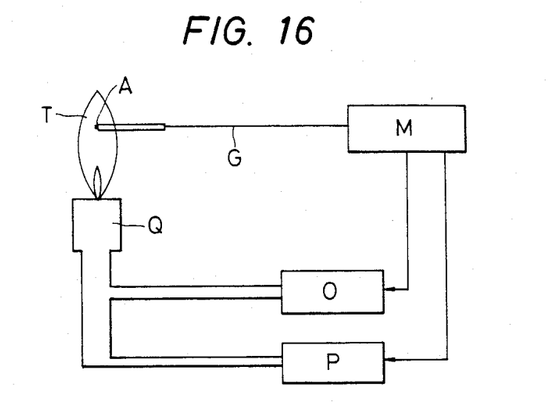
FIG. 16 is a schematic view showing an example in which the gas sensor of the present invention is incorporated into a combustion safety system.

The gas sensor of the present invention can also be applied to a combustion safety device which is shown in FIG. 16. In this example of application, the signal from the element A or the sensor is fed through the cable G to the control circuit M, by which a air blower O or a fuel feeder P is controlled so that the combustion may be complete at all times. The combustion is stopped either in case the complete combustion level is not reached even if the control is conducted by the air blower O and the fuel feeder P or in the case of the misfire. Incidentally, letters Q and T indicate a burner and a flame, respectively.

EXAMPLE 5

The gas sensor of the present invention can also be applied to such an internal combustion engine as is shown in FIG. 17. The element of the sensitive sensor is attached to the exhaust manifold such that the silicon cable G is held and fixed on the body base or a car body V by means of a cable holding member U and connected with or led to the control circuit M or another controller by means of a connector W. Moreover, letter $X_1$ indicates a combustion chamber; letter $X_2$ indicates an igntion plug; letter $X_3$ indicates an air pump; letter $X_4$ indicates a fuel injection pump; letter $X_5$ indicates a mixing chamber; letter Y indicates an exhaust manifold; letter $Z_1$ indicates a catalyzer muffler; and letter $Z_2$ indicates an exhaust port.

EXAMPLE 6

Figure 18:
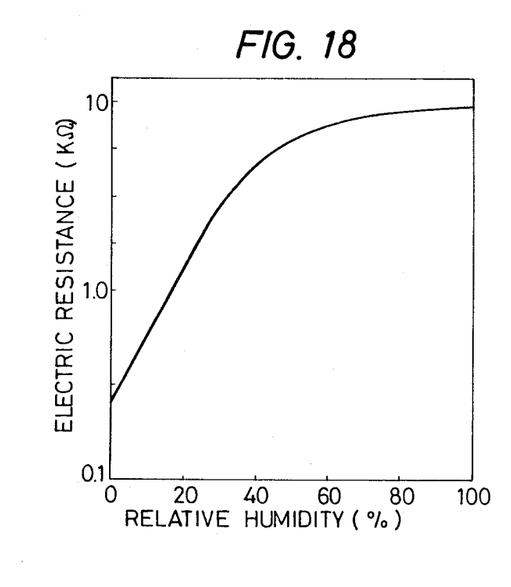
FIG. 18 is a humidity sensitive characteristic diagram of the gas sensor used as a humidity sensor of Example 1 of the present invention.

FIG. 18 shows an example in which the gas sensor produced as the sample (f) of the Example 1 is applied as a humidity sensor. In view of FIG. 18, it is found that the electric resistance is abruptly changed in a linearly manner for the relative humidity equal to or less than 50% and that the gas sensor is effective for the humidity sensor.

What is claimed is:
1. A gas sensor comprising:
   an electrically insulating base;
   electrodes formed on said base; and
   a gas sensitive film being formed on the surface of said base at a portion, where the film detects a gas to be sensed and the film electrically contacts said electrodes;
   said gas sensitive film being formed of a thermal-sprayed film of a semiconductor oxide having a perovskite structure with fine cracks therein by plasma spray coating powders of a perovskite structure oxide having a particle size equal to or smaller than 25 μm.
2. A gas sensor according to claim 1, wherein said thermal-sprayed film is prepared by plasma spray coating powders of a perovskite structure oxide having a particle size equal to or smaller than 5 μm and is formed with fine cracks.
3. A gas sensor according to claim 1 or 2, wherein said thermal-sprayed film is prepared by holding said electrically insulating base at a temperature equal to or higher than 500° C.
4. A gas sensor comprising:
   an electrically insulating base comprising a thin plate at least a surface of which is formed of alumina;
   electrodes formed on said base; and
   a gas sensitive film formed on the surface of said base at a portion, where the film detects a gas to be sensed and the film electrically contacts the electrodes; said gas sensitive film being a thermal-sprayed film of a semiconductor oxide having a perovskite structure of $LaNiO_3$ with fine cracks formed therein by plasma spray coating of powders of $LaNiO_2$ having a particle size equal to or smaller than 5 μm directly on said electrically insulating base held at a temperature higher than 500° C. during the plasma spray coating.
5. A gas sensor comprising:
   an electrically insulating base comprising a thin plate;
   electrodes formed in pairs on major surfaces of said plate; and
   a gas sensitive film formed on the surface of said base at a position where the film contacts a gas to be sensed;
   said gas sensitive film being a thermal-sprayed film of an oxide having a perovskite structure with fine cracks formed therein and being formed as said gas sensitive film between the electrodes of one pair by plasma spray coating a powder of a perovskite structure oxide having particle sizes equal to or smaller than 5 μm, and
   a film having at least one of thermistor and heater characteristics being formed to be in electric contact with the electrodes of the other pair.
6. A gas sensor according to claim 5 wherein said thermal-sprayed film is prepared by holding said electrically insulating base at a temperature equal to or higher than 500° C.
7. A gas sensor according to claim 1, 4, or 5 wherein said oxide having the perovskite structure is a P-type semiconductor.
8. A gas sensor according to claim 1, 4 or 5 wherein said electrically insulating base has its surface made porous at least beneath said gas sensitive film.
9. A gas sensor according to claim 1, 4 or 5, wherein said thermal-sprayed film consists of the perovskite structure oxide.
10. A gas sensor according to claim 1, 4 or 5, wherein said electrically insulating base is a thin plate which is made of a highly thermally conductive material having a thickness equal to or smaller than 0.5 mm.
11. A gas sensor according to claim 1 or 5, wherein said highly thermally conductive material is selected from the group consisting of alumina and silicon carbide.
12. A gas sensor according to claim 1 or 5, wherein said oxide having the perovskite structure is selected from the group consisting of $LaNiO_3$, $La_2CuO_4$, $CeTiO_3$, $PrTiO_3$, $NdTiO_3$, $LaTiO_3$, $LaCrO_3$, $La_{1-x}Sr_xCoO_3$ ($0.1 \leq x \leq 0.5$) and $La_{1-x}Sr_xVO_3$ ($0 \leq x \leq 0.5$).

* * * * *